US012693207B1

(12) United States Patent
Houston et al.

(10) Patent No.: US 12,693,207 B1
(45) Date of Patent: Jul. 28, 2026

(54) DIRECT FLOW CELL MOUNTABLE SPECTROSCOPY SYSTEM WITH INTERNAL GAS CELL

(71) Applicant: KineoLabs, Inc., Billerica, MA (US)

(72) Inventors: J. Grant Houston, Lexington, MA (US); Walid A. Atia, Jamaica Plain, MA (US)

(73) Assignee: KineoLabs, Inc., Billerica, MA (US)

( * ) Notice: Subject to any disclaimer, the term of this patent is extended or adjusted under 35 U.S.C. 154(b) by 8 days.

(21) Appl. No.: 18/626,871

(22) Filed: Apr. 4, 2024

Related U.S. Application Data

(60) Provisional application No. 63/495,620, filed on Apr. 12, 2023.

(51) Int. Cl.
G01N 15/1434 (2024.01)
G01N 33/00 (2006.01)

(52) U.S. Cl.
CPC ..... G01N 15/1436 (2013.01); G01N 33/0027 (2013.01)

(58) Field of Classification Search
CPC ........... G01N 15/1436; G01N 33/4915; G01N 21/39; G01N 33/0027; G01J 3/00
See application file for complete search history.

(56) References Cited

U.S. PATENT DOCUMENTS

| | | | | |
|---|---|---|---|---|
| 7,027,470 B2 * | 4/2006 | May | ...................... | H01S 5/0687 |
| | | | | 372/20 |
| 7,567,607 B2 * | 7/2009 | Knowles | ............... | H01S 3/2333 |
| | | | | 372/55 |
| 7,764,379 B1 * | 7/2010 | McDermott | .......... | G01J 3/4338 |
| | | | | 356/437 |
| 7,969,576 B1 * | 6/2011 | Buckley | ................. | G01N 21/39 |
| | | | | 356/437 |
| 8,164,748 B1 * | 4/2012 | Flanders | ................. | G01J 3/108 |
| | | | | 356/300 |
| 2010/0169027 A1 * | 7/2010 | Hu | ........................... | G01N 21/39 |
| | | | | 702/135 |
| 2011/0299076 A1 * | 12/2011 | Feitisch | ............. | G01N 21/3504 |
| | | | | 356/326 |
| 2012/0033220 A1 * | 2/2012 | Kotidis | ................... | G02B 21/06 |
| | | | | 356/445 |
| 2016/0209325 A1 * | 7/2016 | Kotidis | ................ | G01N 21/272 |

FOREIGN PATENT DOCUMENTS

EP                    2520925 A1 *  11/2012   ............. G01N 21/39

* cited by examiner

*Primary Examiner* — Abdullahi Nur
(74) *Attorney, Agent, or Firm* — HoustonHogle LLP

(57) ABSTRACT

Tunable or swept cat's-eye lasers for spectroscopy that is adapted for direct mounting to a flow cell and/or includes an internal gas cell.

19 Claims, 3 Drawing Sheets

Direction of Gas Flow

DIRECT FLOW CELL MOUNTABLE SPECTROSCOPY SYSTEM WITH INTERNAL GAS CELL

RELATED APPLICATIONS

This application claims the benefit under 35 USC 119 (e) of U.S. Provisional Application No. 63/495,620, filed on Apr. 12, 2023, which is incorporated herein by reference in its entirety.

BACKGROUND OF THE INVENTION

Absorption spectroscopy measures the presence and/or concentration of a species of interest in a sample by passing a light beam through the sample and detecting the absorption at wavelengths of a particular spectral absorption feature of the species of interest. Generally, such a feature is an absorption line that represents the frequency of light corresponding to vibrational, rotational or electronic transitions of molecules of the gas or liquid of interest. Tunable diode lasers provide many advantages for such absorption spectroscopy measurements in that the lasers can be tuned to the center of a spectral feature and generate a narrow signal relative to the width of the spectral feature.

Laser absorption spectroscopy can thus offer high speed and relatively high precision capabilities for detecting a variety of trace species in gas or liquid samples. Tunable diode laser spectrometers are particularly suited to high sensitivity studies, in part, because they may be frequency-modulated to reduce low frequency laser noise and electronic noise. In general, a laser spectrometer will include a frequency tunable laser that generates an illumination output beam which is directed through a sample cell that contains a sample. The output beam is then directed to an optical detector and the signal of the optical detector is demodulated to obtain an absorption induced signal. This absorption induced signal can be used to identify one or more species of interest within the sample.

SUMMARY OF THE INVENTION

The present invention concerns a tunable or swept laser architecture that is appropriate for applications including spectroscopy.

The swept laser preferably employs a cat's-eye configuration with a preferably transmissive tilt tuned filter. It can be bolted directly to a flow cell in a sealed connection. In a current example, it includes an internal sealed gas cell such as a cell containing methane at atmospheric temperature. The spectra from the cell are compared to the sample spectra for precise identification.

In general, according to one aspect, the invention features a tunable laser spectroscopy system, comprising a base including a port through the base, a tunable laser implemented on the base and a kinematic mount installed on the base and carrying a mirror. The output beam from the tunable laser is reflected by the mirror to travel through the port to a flow cell.

The laser preferably includes a gain chip mounted on a thermoelectric cooler within a butterfly package. An amplitude reference beamsplitter can reflect a portion of the light to an amplitude reference detector. Often, the kinematic mount includes adjustment bolts for adjusting the tip and tilt of the mirror in two axes of the kinematic mount.

The system usually further comprises a sample detector assembly for holding a sample detector for detecting the output beam after being modulated by the sample in the flow cell.

In general, according to another aspect, the invention features a tunable laser spectroscopy system comprising a tunable laser, an optical bench including an amplitude reference detector and a wavelength reference detector. A gas cell is further placed before the wavelength reference detector.

This gas cell might contains methane.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Also, all conjunctions used are to be understood in the most inclusive sense possible. Thus, the word "or" should be understood as having the definition of a logical "or" rather than that of a logical "exclusive or" unless the context clearly necessitates otherwise. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figures 1, 2A, 2B, 2C:
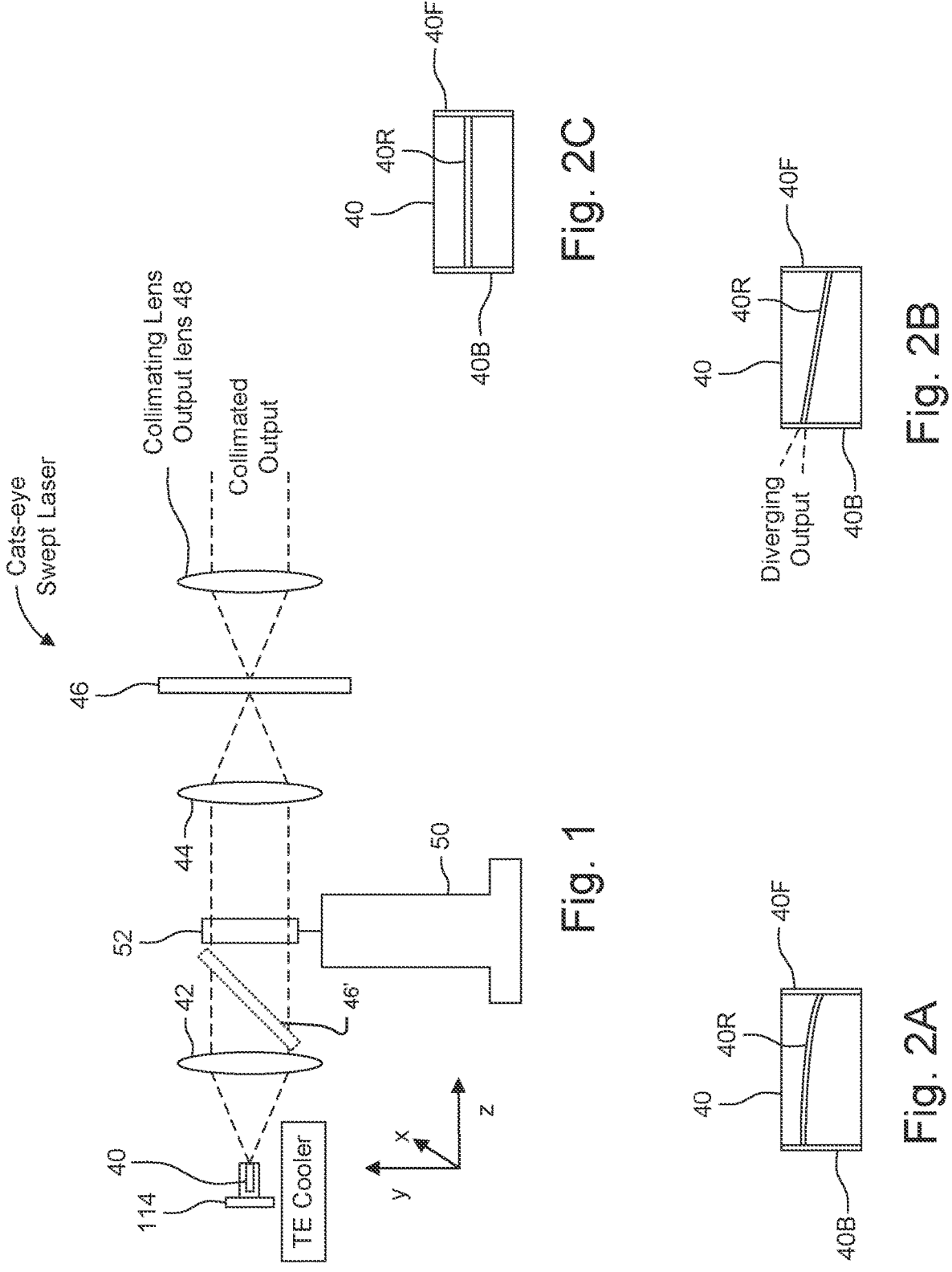
FIG. 1 is a schematic side view of a cat's-eye tunable laser according to the present invention.
FIGS. 2A, 2B, and 2C are schematic top views of gain chips for different tunable lasers.

FIG. 1 shows a cat's-eye swept or tunable laser, which is one laser architecture compatible with the disclosed tunable laser spectroscopy system.

The laser's amplification is provided by an InP gain chip 40. In one example, the gain chip amplifies light in the wavelength range of about 1500-1800 nanometers.

Preferably its center wavelength is around 1700 nanometers+/−50 nanometers or more generally +/−100 nanometers.

Other material systems can be selected for the gain chip, however, when other wavelength ranges are needed. Common material systems are based on III-V semiconductor materials, including binary materials, such as GaN, GaAs, InP, GaSb, InAs, as well as ternary, quaternary, and pentenary alloys, such as InGaN, InAlGaN, InGaP, AlGaAs, InGaAs, GaInNAs, GaInNAsSb, AlInGaAs, InGaAsP, AlGaAsSb, AlGaInAsSb, AlAsSb, InGaSb, InAsSb, and InGaAsSb. Collectively, these material systems support operating wavelengths from about 400 nanometers (nm) to 2500 nm, including longer wavelength ranges extending into multiple micrometer wavelengths. Semiconductor quantum well, quantum cascade and quantum dot gain regions are typically used to obtain especially wide gain and spectral emission bandwidths, and support operation up to 250 μm in wavelength. Quantum well layers may be purposely strained or unstrained depending on the exact materials and the desired wavelength coverage.

In the preferred embodiment, the gain chip might be mounted in a package 114 such as a TO-can type hermetic package, although a butterfly package is shown. These packages protect the chip from dust and the ambient environment including moisture. In some examples, the TO-can or butterfly package has an integrated or a separate thermoelectric cooler.

The free space beam from the package 114 is diverging in both axes (x, y). It is collimated by a collimating lens 42. The resulting collimated beam is received by a cat's eye focusing lens 44, which focuses the light onto a cat's eye mirror/output coupler 46. This defines the other end of the laser cavity, extending between the mirror/output coupler and the back/reflective facet of the gain chip.

Other output couplers can be used for extracting light from the cavity. For example, a 45 degree angle partially reflecting mirror 46' is alternatively used on some examples. The mirror 46' is often located between the collimating lens 42 and bandpass filter 52.

The collimated light between the collimating lens and the cat's eye focusing lens passes through the bandpass filter 52 that is angle-tuned in the beam by a galvanometer 50 or other actuator.

In the present design, the free spectral range of the tunable filter 52 is preferably greater than 200 nanometer and is preferably over 300 nm such as about 350 nm.

The so-called "effective refractive index" of the tunable filter 52 is preferably greater than 1.50, and is ideally higher than 1.60, such as 1.65.

The passband for the filter is preferably between 1 and 3 nanometers (nm), and more narrowly between 1.5 and 2.5 nm, FWHM. In one design, it is 2 nm. But, in operation, linewidth narrowing (~4×) reduces this in the laser cavity for the effective laser linewidth.

These general design parameters yield a large number of modes under the envelope for the filter linewidth for a laser cavity length of 50 mm. In the preferred embodiment, there are at least 15 modes under the filter envelope and at least 5 modes for linewidth narrowed to 0.5 nm. Ideally, there are at least 25 modes and possibly 37 modes or more and at least 7 modes or 10 or more modes for linewidth narrowed.

This is a large number of modes that will work well for low noise spectral analysis. And keep in mind that the larger the number of modes, the lower the modal noise (by sqrt (number of modes). However, the amplitude referencing takes out amplitude noise through common mode noise rejection either by digital division or constant power control while sweeping over the tuning range.

The bandpass filter is held on an arm of the galvanometer 50. This allows for tilting of the bandpass filter in the collimated beam to thereby tilt tune the filter and thus change the passband to scan or sweep the wavelength of the swept laser.

Tuning speed specifications for galvanometer generally range from 0.1 Hz to 50 KHz. For the higher speeds, a 25 kHz resonant galvo can be used with bi-directional tuning, but higher and lower speeds can be used. Wavelength tuning speed is usually given in nm/sec. In general, the tuning speed should be between 3000 nm/sec 11000 nm/sec.

The size of the collimated beam is important for many applications. As a general rule, a smaller beam results in higher divergence resulting in a larger cone half angle (CHA), which is the divergence of the beam hitting the tunable filter. This reduces the minimum line width over angle for a tunable filter. In the current embodiment, the CHA must be smaller than a given amount, typically 0.025 degrees, in order to maintain both linewidth and loss.

This is a plot of percent transmission as a function of wavelength for different values for CHA for the S polarization.

Note that a higher divergence beam has a smaller diameter, so this means that to have collimated beams of a large enough diameter to provide the required maximum CHA, physically larger tunable filters are required. A beam size of ~1 millimeters (mm) is typical for a CHA of 0.025 degrees, but because the beam from the chip is elliptical this should be chosen to be the smaller axis beam). Moreover, the final output collimating lens 48 forms a telescope from the cat's eye focusing lens 44 to have an output beam of whatever desired diameter, with the magnification given by the ratio of the output lens focal length to the focusing lens focal length. Note that if desired the elliptical output beam is circularized with the use of anamorphic prism pairs, a pair of cylindrical lenses, or a simple spatial filter at the output, in different examples.

In any event, the beam size for the small axis at the tunable filter is preferably between 0.5 and 2 mm.

The light from the gain chip is polarized. In the common architectures, the polarization is horizontal or parallel to the epitaxial layers of the edge-emitting gain chip. In the preferred configuration, the filter is oriented to receive the S polarization in order to maintain narrow line width of the filter as it is tilt tuned. On the other hand, the P polarization broadens drastically at large tilt angles. S polarization has higher loss at larger tilt angles than P. So, the filter design needs to address these issues by providing a low enough loss across the tuning band for S.

In general, the present cat's-eye configuration provides a number of advantages. It provides low loss, low tolerance, repeatable stable operation since lower angle wavelength change over grating-based lasers.

The mirror/output coupler 46 will typically reflect less than 90% and preferably about 80% of the light back into the laser's cavity and transmits greater than 10% and preferably about 20% of light. Often, the transmitted light is collimated with the help of an output collimating lens 48. More generally, the mirror/output coupler can reflect from 10% to 99% of light (transmitting 90% to 1%, respectively), depending on the output power and laser cavity loss desired. Higher reflectivity results in lower loss cavities and thus wider laser tuning range where gain exceeds loss, but results in lower output power.

FIG. 2A shows a preferred gain chip 40. The chip is termed a single angled facet (SAF) edge-emitting chip. As such, it has a high reflectivity (HR) coated rear facet 40B. It has an antireflective (AR) coated front facet 40F. In addition, for improved performance, it has a curved ridge waveguide 40R that is perpendicular to the rear facet but is angled at the interface with the front facet. This angling at the front facet along with the AR coating reduces reflections at the front facet reflectivity by up to 40 dB and significantly improves laser performance by reducing parasitic reflections that can otherwise lead to non-smooth tuning and mode-hopping.

FIG. 2B shows another potential edge emitting gain chip 40. The basic configuration is termed a SOA gain chip. As such, it has an HR coated rear facet 40B and an AR coated front facet 40F. Here again, the straight ridge waveguide 40R intersects with the front facet at an angle to minimize reflections back into the chip. In one example, its back facet is used as the laser's output. As such the back facet reflectivity is about 80% of the light back into the laser's cavity and transmits about 20% of light.

FIG. 2C shows another potential gain chip 40. The basic configuration is termed a Fabry-Perot gain chip. As such, it has an HR coated rear facet 40B and an AR coated front facet 40F. The straight ridge waveguide 40R intersecting with the front facet at perpendicular does create some internal reflections that can affect performance.

Figure 3:
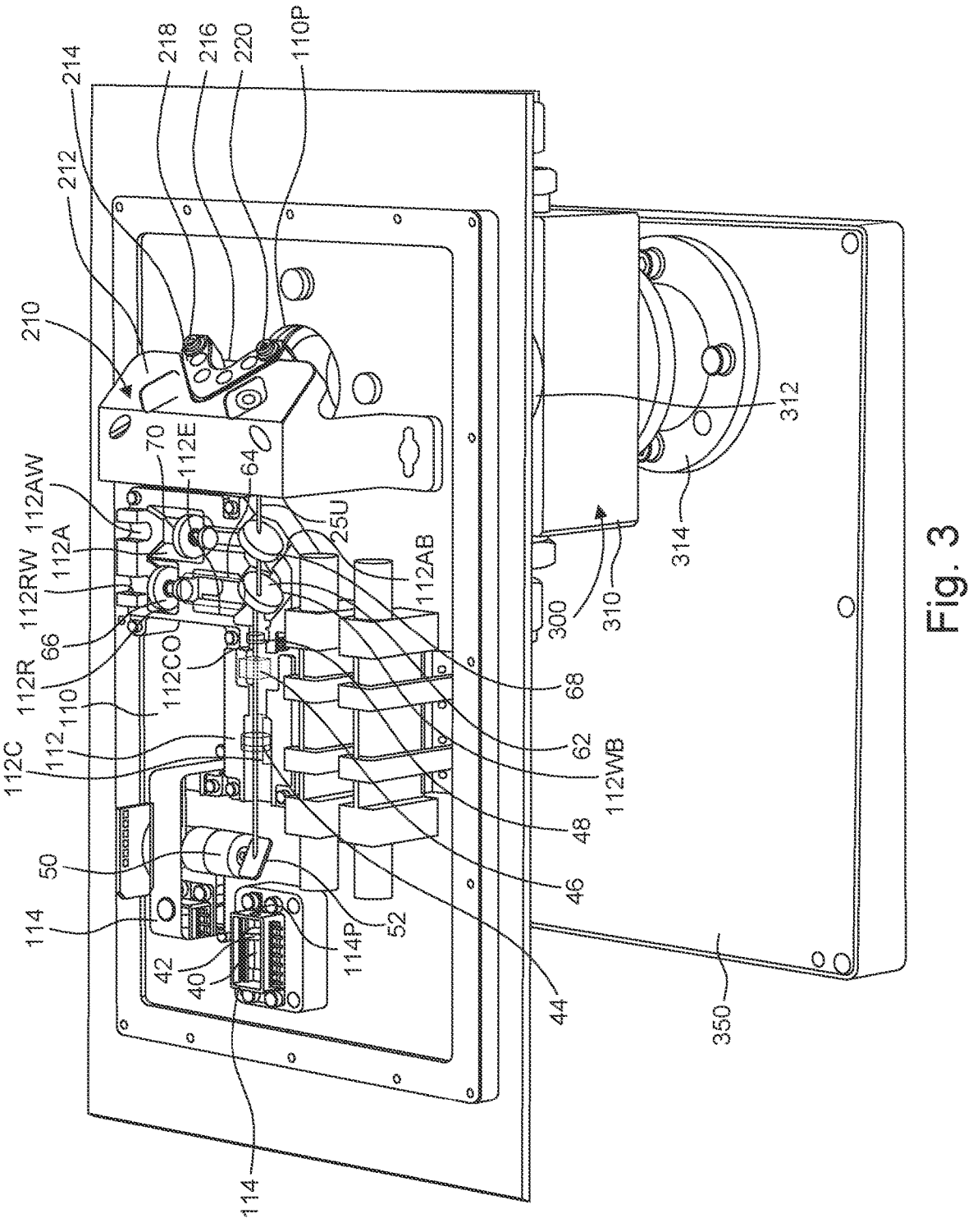
FIGS. 3 and 4 are different perspective views of a tunable laser spectroscopy system with the cat's-eye swept connected to a flow cell.

FIG. 3 is a perspective view of a tunable laser spectroscopy system with a cat's-eye swept or tunable laser according to the invention. Here, it is shown connected to a flow cell, sample cell, or other liquid sample holder 300.

The gain chip 40 in this example is mounted on a thermoelectric cooler within a butterfly package 114. The package includes a front windowed port 114P. The light generated by the gain chip 40 is collimated by the collimating lens 42, here located inside the package 114, to pass through the windowed port. Preferably a window is bonded in the port. The window is preferably AR coated to be transmission to the wavelength of operation of the system.

In the illustrated example, the chip is InP. Such chips generally provide gain in the 1200 to 1800 nm band. In the illustrated example, the system is intended to cover the CH band extending from about 1500 to 1800 nm.

The beam then propagates to the thin film interference filter 52. The cats-eye focusing lens 44 focuses the beam onto the cats-eye mirror/output coupler 46 after being transmitted through the filter 52. Preferably, the cats-eye focusing lens 44 is compound or achromatic doublet lens to ensure good focus across the wavelength of operation.

The beam passing through the output coupler 46 is collimated by output collimating lens 48 and the collimated beam is received by a gas cell beamsplitter 62. This reflects a portion of the beam, such as a few percent to gas cell 64. The transmitted light is then detected by a gas cell detector 66.

The gas cell 64 is employed for calibration for the detection of the same or similar gas by the system.

In other embodiments, the gas cell is replaced by a different gas cell. Currently, the system is intended to quantify the concentration of methane, so methane is contained in the gas cell 64, but other gases or mixtures of gases can be contained in the cell. In still another example, the gas cell is replaced with a wavelength reference such as an etalon.

The light not reflected by the gas cell splitter 62 passes to a second beam splitter, amplitude reference beamsplitter 68. This reflects a portion of the beam, again a few percent usually, to an amplitude reference detector 70.

The system is supported on a base 110 such as a metal plate. A butterfly pedestal 110P holds the butterfly package 114 on the base 110.

An optics frame 112 is mounted to the base 110. In one example, this is 3D printed using a filament-fed, FDM 3D printer or a MSLA (Masked Stereolithography) resin 3D printer.

For holding the various components, it has a series of cradles or V-groove optical element mounting locations formed into the top surface of the optical bench or frame 112. These include cats-eye focusing lens v-groove cradle 112C, collimating output lens cradle 112CO, a gas cell beamsplitter cradle 112WB, amplitude reference beamsplitter cradle 112AB, gas cell cradle 112E, gas cell detector cradle 112R, amplitude detector cradle 112A, gas cell wire port 112RW, amplitude wire port 112AW.

Finally, galvanometer clamp 114 secures the galvanometer 50 to the base 110.

In the illustrated example, the output beam 25U is reflected to pass through a port 110P in the base 110. This configuration allows the system to be mounted to and directly bolted to a flow cell assembly and make an air tight and/or liquid tight seal with that flow cell assembly.

The output beam 25U is reflected by an output mirror assembly 210. It comprises a output bracket 212 that is bolted to the base 110 and forms a U-shaped bridge extending over the output beam 25U.

The bracket or mount 212 holds a kinematic mount 214 that holds a mirror 216 in the path of the output beam 25U. The kinematic mount 214 has two adjustment bolts 218, 220 that are used to adjust the tip and tilt of the mirror 216 in the two axes of the kinematic mount 214.

The reflected output beam passes into the flow cell assembly 300. In particular, the flow cell assembly 300 includes a flow cell 310 and two bobbin shaped standoffs 312, 314.

A sample detector assembly 350 holds the sample detector for detecting the output beam 25U after being modulated by the sample in the flow cell 310.

Figure 4:
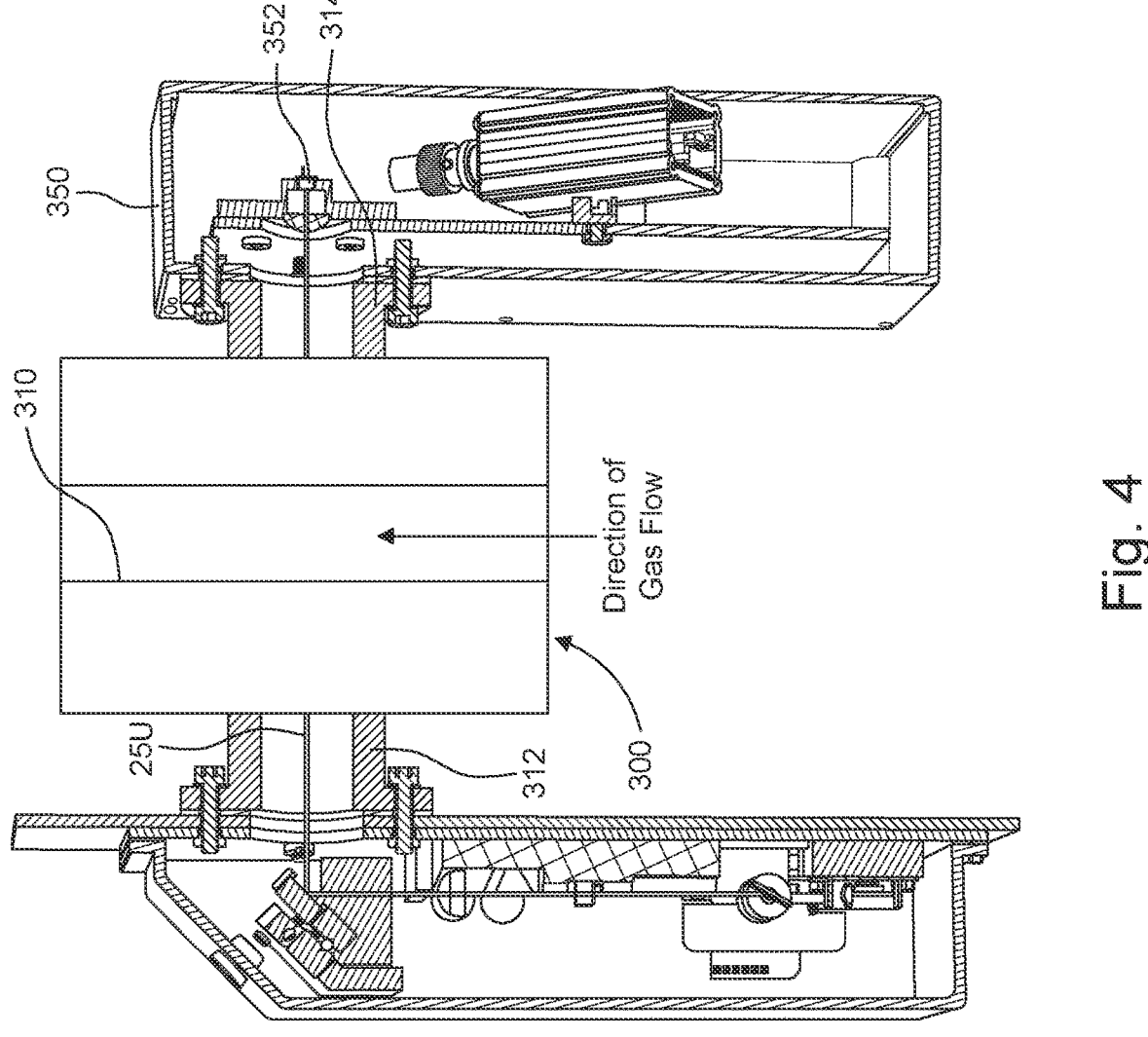

FIG. 4 shows the tunable laser spectroscopy system and flow cell assembly in cross-section.

The output beam 25U is reflected by an output mirror assembly 210. It comprises a mount 212 that is bolted to the base 110 and forms a U-shaped bridge extending over the output beam 25U.

The bracket 212 holds the kinematic mount 214 that holds the mirror 216 in the path of the output beam 25U. The kinematic mount's two adjustment bolts 218, 220 are used to adjust the tip and tilt of the mirror 216 in the two axes of the kinematic mount 214 to align the beam 25U onto the detector 352.

The reflected output beam passes into the flow cell assembly 300. In particular, the flow cell assembly 300 includes a flow cell 310 and two bobbin shaped standoffs 312, 314.

A sample detector assembly 350 holds the sample detector 352 for detecting the output beam 25U after being modulated by the sample in the flow cell 310.

While this invention has been particularly shown and described with references to preferred embodiments thereof, it will be understood by those skilled in the art that various changes in form and details may be made therein without departing from the scope of the invention encompassed by the appended claims.

What is claimed is:

1. A tunable laser spectroscopy system, comprising:
a base including a port through the base;
a tunable laser implemented on the base; and
kinematic mount installed on the base and carrying a mirror;
wherein an output beam from the tunable laser is reflected by the mirror to travel through the port to a flow cell.

2. The tunable laser spectroscopy system as claimed in claim 1, wherein the laser includes a gain chip mounted on a thermoelectric cooler within a butterfly package.

3. The tunable laser spectroscopy system as claimed in claim 1, further comprising an amplitude reference beamsplitter for reflecting a portion of the light to an amplitude reference detector.

4. The tunable laser spectroscopy system as claimed in claim 1, wherein the kinematic mount includes adjustment bolts for adjusting the tip and tilt of the mirror in two axes of the kinematic mount.

5. The tunable laser spectroscopy system as claimed in claim 1, further comprising a sample detector assembly for holding a sample detector for detecting the output beam after being modulated by the sample in the flow cell.

6. The tunable laser spectroscopy system of claim 1, wherein the gain chip is InP and provides gain in the 1200 to 1800 nm band.

7. The tunable laser spectroscopy system of claim 1, wherein the system is intended to quantify the concentration of methane.

8. The tunable laser spectroscopy system of claim 1, wherein the base is a metal plate.

9. A tunable laser spectroscopy system, comprising:
a tunable laser;
an optical bench including a amplitude reference detector, and a wavelength reference detector; and
a gas cell before the wavelength reference detector.

10. The tunable laser spectroscopy system of claim 9, wherein the gas cell contains methane.

11. The tunable laser spectroscopy system of claim 1, wherein the base is configured to be mounted directly to a flow cell assembly.

12. The tunable laser spectroscopy system of claim 11, wherein the base is directly bolted to the flow cell assembly.

13. The tunable laser spectroscopy system of claim 11, wherein the base and the flow cell assembly form an air-tight seal.

14. The tunable laser spectroscopy system of claim 11, wherein the base and the flow cell assembly form a liquid-tight seal.

15. The tunable laser spectroscopy system of claim 1, further comprising an output mirror assembly including a bracket bolted to the base.

16. The tunable laser spectroscopy system of claim 15, wherein the bracket forms a U-shaped bridge extending over the output beam.

17. The tunable laser spectroscopy system of claim 15, wherein the kinematic mount is held by the bracket.

18. The tunable laser spectroscopy system of claim 5, wherein the sample detector assembly is arranged on an opposite side of the flow cell from the base such that the output beam passes through the flow cell before reaching the sample detector.

19. The tunable laser spectroscopy system of claim 9, further comprising a gas cell beamsplitter positioned in an output beam path and configured to reflect a portion of the output beam into the gas cell, and a gas cell detector positioned to detect light transmitted through the gas cell, wherein the gas cell contains methane and absorption spectra produced by the gas cell are compared to sample spectra to perform wavelength calibration.

\*  \*  \*  \*  \*